(12) United States Patent
Nelson et al.

(10) Patent No.: US 8,741,109 B2
(45) Date of Patent: *Jun. 3, 2014

(54) METHOD FOR PURIFYING ACETONE

(75) Inventors: Mark Erik Nelson, Mount Vernon, IN (US); Andrey Yurievich Sokolov, St. Petersburg (RU); Ilya Yurievich Krupenko, St. Petersburg (RU); Valery Yurievich Aristovich, St. Petersburg (RU)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 542 days.

This patent is subject to a terminal disclaimer.

(21) Appl. No.: 12/633,746

(22) Filed: Dec. 8, 2009

(65) Prior Publication Data
US 2010/0140075 A1    Jun. 10, 2010

(30) Foreign Application Priority Data

Dec. 9, 2008  (RU) ................................ 2008148186

(51) Int. Cl.
*B01D 3/42* (2006.01)
*B01D 3/34* (2006.01)
*C07C 45/82* (2006.01)
*C07C 45/85* (2006.01)
*C07C 49/08* (2006.01)

(52) U.S. Cl.
USPC ............ 203/2; 203/1; 203/3; 203/31; 203/33; 203/36; 203/73; 203/80; 568/411

(58) Field of Classification Search
USPC ............ 203/1–3, 31, 33, 36, 73, 80; 568/411
See application file for complete search history.

(56) References Cited

U.S. PATENT DOCUMENTS

| 1,542,538 | A | * | 6/1925 | Willkie | 568/411 |
| 3,215,745 | A |   | 11/1965 | Frank | |
| 4,329,510 | A | * | 5/1982 | Uno et al. | 568/411 |
| 4,336,109 | A | * | 6/1982 | Hosaka et al. | 203/34 |

(Continued)

FOREIGN PATENT DOCUMENTS

CA    1016100    8/1977

OTHER PUBLICATIONS

PCT International Search Report for International Application No. PCT/US2009/067296.

(Continued)

*Primary Examiner* — Virginia Manoharan
(74) *Attorney, Agent, or Firm* — Michael Best & Friedrich LLP

(57) ABSTRACT

A method for purifying a crude acetone raw material containing low molecular weight impurities using two columns is disclosed. Crude acetone raw material is fed into a first column; adding an alkaline reagent and an oxidative agent into the first column to form high molecular weight impurities; removing a top fraction from the first column by distillation to form bottom fraction containing an acetone mixture containing high molecular weight impurities; feeding the bottom fraction containing the acetone mixture obtained to a second rectification column at a charge point on the column; adding an alkaline reagent to the second column above the charge point of the bottom fraction fed; and separating a purified acetone from the high molecular weight impurities and removing the purified acetone as a top fraction by distillation in the second column, wherein the second rectification column is operated at atmospheric pressure.

3 Claims, 1 Drawing Sheet

(56) References Cited

U.S. PATENT DOCUMENTS

| | | |
|---|---|---|
| 4,340,447 A | 7/1982 | Laverick et al. |
| 4,722,769 A | 2/1988 | Chan et al. |
| 5,788,818 A * | 8/1998 | Lorenzoni et al. ............ 203/17 |
| 6,340,777 B1 | 1/2002 | Aristovich et al. |
| 7,416,645 B2 * | 8/2008 | Weber et al. ............ 568/411 |
| 8,058,479 B2 * | 11/2011 | Nelson et al. ............ 568/411 |

OTHER PUBLICATIONS

PCT Written Opinion of the International Searching Authority for International Application No. PCT/US2009/067296.

* cited by examiner

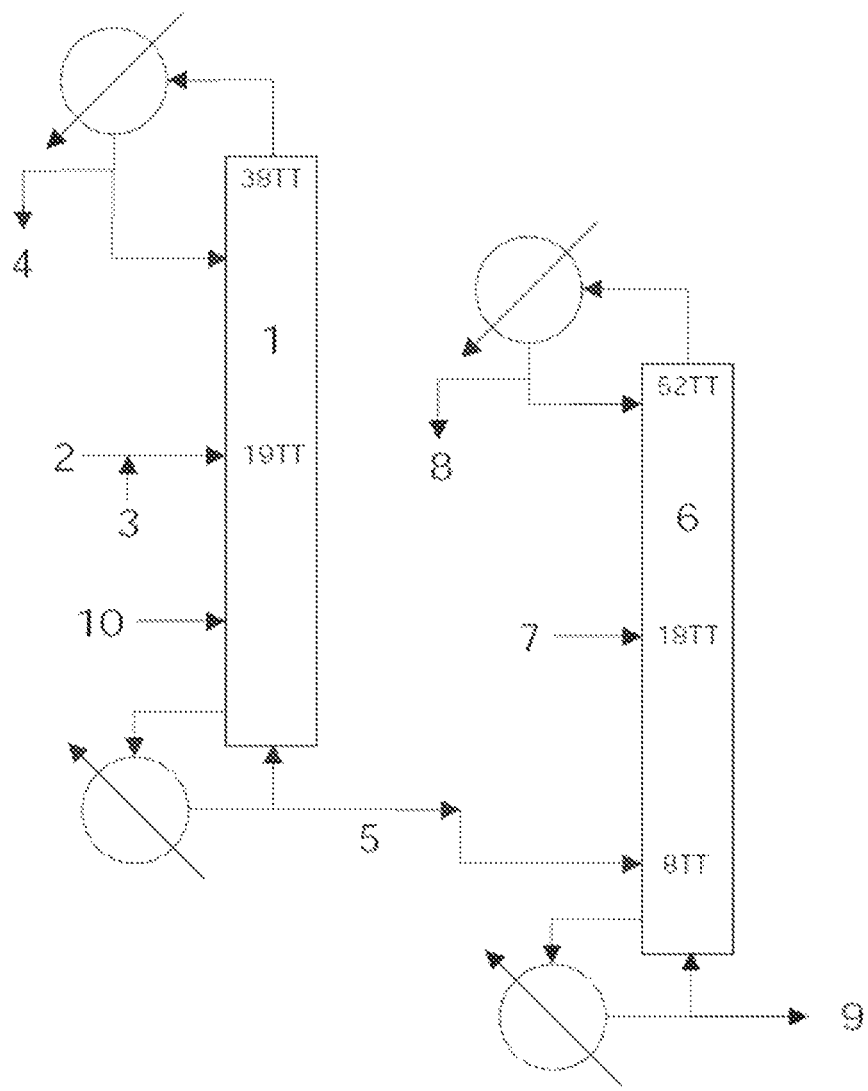

8,741,109 B2

METHOD FOR PURIFYING ACETONE

CROSS REFERENCE TO RELATED APPLICATIONS

This application claims priority to Russian Application Serial No. 2008148186, filed Dec. 9, 2008. This disclosure is hereby fully incorporated herein by reference. This application is related to 08LEX0022-US-NP entitled "METHOD FOR PURIFYING ACETONE" and filed on Dec. 8, 2009. This related application is hereby incorporated by reference in its entirety.

BACKGROUND

The present invention relates to the field of chemistry and, specifically, to the technology of organic synthesis; namely to the production of acetone obtained together with phenol during the decomposition of cumene hydroperoxide.

In addition to the basic products, which are acetone and phenol, an entire series of impurities having an adverse effect on the quality of the end product forms during the oxidation of cumene and subsequent decomposition of cumene hydroperoxide. After neutralization, acetone and phenol, the decomposition products of cumene hydroperoxide are fed to a fractionation column, in which they are separated into acetone raw material and phenol raw material fractions. Then, depending on the purification system used, the acetone raw material and phenol raw material fractions enter the appropriate stages of isolation and purification.

A method is known for purifying acetone raw material comprising subjecting the decomposition product to purification in two rectification columns wherein the acetone treated in the first rectification column is sent to the second rectification column, and purified acetone is discharged from the top of the second rectification column as a commercial product (see U.S. Pat. No. 3,215,745).

It is known, however, that use of simple distillation methods alone to purify acetone raw material is not completely effective since impurities, specifically, aliphatic aldehydes, olefins and a whole series of other impurities, remain in the treated acetone product, reducing its purity and quality.

Another known method of purifying acetone is a method in which acetone raw material is distilled in two columns. In this method, low molecular weight impurities are isolated in the first rectification column with the addition of an alkaline reagent to the first column. The remaining mixture of components (the still or bottom residues from the first rectification column) are subsequently sampled and charged or fed to the second rectification column in order to separate high molecular weight impurities and isolate purified, commercial acetone (see U.S. Pat. No. 6,340,777). In the method just described, it is possible to produce product acetone with a KT-test time of at least 5 hours when operating under optimum conditions. A disadvantage of this method is that the second rectification column operates at pressures below atmospheric pressure, which markedly increases operating costs and also significantly reduces the productivity of the second column compared to a column operated at atmospheric pressure (for example, it can reduce productivity up to 50% compared to a column with everything else being the same except operating pressure). Therefore, this method may produce acetone where the quality is not as high and/or the operating costs are higher and the productivity of the facility is lower due to the lower operating pressure. This is due to the use of the vacuum column to keep the aldol reversion reaction from occurring; there will be aldol reversion at atmospheric pressure.

There is a need to provide a simple and flexible method for further purifying acetone (to reduce the levels of impurities) without regard to the quality of the acetone raw material.

SUMMARY OF THE INVENTION

The inventors have found that it is possible to produce high-quality acetone with maximum utilization of equipment and reagents and minimal capital expenditures for modernization. Some or all of the above-described deficiencies are addressed by a method for purifying a crude acetone raw material containing low molecular weight impurities, using two columns in sequence comprising the steps of: a) feeding the crude acetone raw material into a first column; b) adding an alkaline reagent and an oxidative agent into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an alkaline reagent to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

In another embodiment, a method for purifying a crude acetone raw material containing low molecular weight impurities, using two columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an aqueous sodium hydroxide solution to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

In yet another embodiment, a method for purifying a crude acetone raw material containing low molecular weight impurities, using two columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an aqueous sodium hydroxide solution to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, wherein the weight ratios of the sodium hydroxide solution to the hydrogen peroxide solution are between 1:0.5 to 1:10, and wherein the weight ratios of the sodium hydroxide solution in the first rectification column to the sodium hydroxide solution in the second rectification column are between 1:0.1 to 1:5, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

It has been discovered that it is possible to produce commercial (purified) acetone with a KT-test time of at least 5 hours, specifically at least 8.5 hours, when operating in optimum conditions. Both the alkaline and oxidative reagents must be added in order for the method to achieve the desired results, but minimal capital expenditures for modernization of existing equipment are needed, making this method desirable. The addition of the oxidative reagent to the first column is a benefit for systems running under both vacuum and those at atmospheric pressure.

BRIEF DESCRIPTION OF THE DRAWING

The FIGURE is a process flow diagram of the two column rectification process of the invention.

DETAILED DESCRIPTION OF THE INVENTION

The inventors have found a way to further reduce the amount of impurities in acetone by a method for purifying a crude acetone raw material containing low molecular weight impurities, using two columns in sequence comprising the steps of: a) feeding the crude acetone raw material into a first column; b) adding an alkaline reagent and an oxidative agent into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an alkaline reagent to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

In embodiments, the alkaline reagent is an organic or an inorganic base. In an embodiment, the alkaline reagent is an aqueous alkaline solution, specifically an aqueous alkaline solution having an alkali salt concentrations of from 0.1 wt % to 30 wt %, more specifically sodium hydroxide. In an embodiment, the alkaline reagent is fed to the first rectification column in amount of from 0.05 wt % to 0.8 wt % of the crude acetone raw material fed to the first column, and the alkaline reagent is fed to the second rectification column in an amount of from 0.03% to 0.5% of the crude acetone raw material fed to the first column.

In an embodiment, the oxidative reagent is an organic or an inorganic oxidative reagent or a combination of one or more organic or inorganic reagents. In an embodiment, the oxidative reagent is selected from the group consisting of hydrogen peroxide, methylhydroperoxide, and cumene hydroperoxide, specifically hydrogen peroxide. In an embodiment, the oxidative reagent is an aqueous solution comprising from 0.1 wt % to 30 wt % oxidative reagent. In another embodiment, the oxidative reagent solution is fed to the first rectification column in an amount of from 0.02 wt % to 0.50 wt % of the crude acetone raw material charge. In an embodiment, the oxidative reagent is an aqueous solution comprising from 0.1 wt % to 30 wt % oxidative reagent and the oxidative reagent solution is fed to the first rectification column in an amount of from 0.02 wt % to 0.50 wt % of the crude acetone raw material charge.

In an embodiment, the purified acetone has an acetaldehyde level of less than 8.1 ppm as measured by gas chromatography from a calibration curve obtained using acetaldehyde/acetone standards. In another embodiment, the purified acetone has KT-Test time of greater than or equal to 9.0 hours, as measured by the SABIC KT-Test method.

In another embodiment, a method for purifying a crude acetone raw material containing low molecular weight impurities, using two columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an aqueous sodium hydroxide solution to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

In yet another embodiment, a method for purifying a crude acetone raw material containing low molecular weight impurities, using two columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a bottom fraction comprising an acetone mixture comprising high molecular weight impurities; d) feeding the bottom fraction comprising the acetone mixture obtained in step c) to a second rectification column at a charge point on the column; e) adding an aqueous sodium hydroxide solution to the second column above the charge point of the bottom fraction fed in step d); and f) separating a purified acetone from the high molecular weight impurities and removing the purified acetone as a top fraction by distillation in the second column, wherein the second rectification column is operated at atmospheric pressure, wherein the weight ratios of the sodium hydroxide solution to the hydrogen peroxide solution are between 1:0.5 to 1:10, and wherein the weight ratios of the sodium hydroxide solution in the first rectification column to the sodium hydroxide solution in the second rectification column are between 1:0.1 to 1:5, and wherein the purified acetone has an acetaldehyde level of less than 10 ppm as measured by gas chromatography from a calibration curve obtained using acetaldehyde/acetone standards and a KT-Test time of greater than 8.5 hours, as measured by the SABIC KT-Test method.

In embodiments, the purified acetone has an acetaldehyde level of less than 8.1 ppm as measured by gas chromatography from a calibration curve obtained using acetaldehyde/acetone standards and a KT-Test time of greater than or equal to 9.0 hours, as measured by the SABIC KT-Test method.

The method of the present invention is a reliable, economical and simple method for removing aldehydes and other unsaturated impurities from acetone raw material, wherein the alkaline and oxidative reagents are used in such quantities that the acetone itself is not subject to their harmful action during production of high quality, purified commercial grade acetone that does not contain aldehydes or contains very low levels of aldehydes.

Both the first and second rectification columns are desirably operated at atmospheric pressure or at a pressure below atmospheric, specifically at atmospheric pressure.

In normal cumene hydroperoxide decomposition that produces acetone and phenol, the acetone raw material contains acetone, water, aldehydes, α,β-unsaturated carbonyls, cumene and alpha-methyl-styrene. The acetone raw material to be purified (containing these impurities) is fed to an purification section of the plant consisting of at least two distillation, columns, for isolation and purification of the acetone. The majority of low-boiling (low molecular weight) acetone impurities, such as the various aldehydes, are removed from the first rectification column in the top fraction. An alkaline reagent is also fed to the first rectification column to convert the remaining portion of aldehydes and α,β-unsaturated carbonyls into high-boiling (high molecular weight) components. The alkaline reagent may be fed into the first rectification column at any desirable point, such as into the raw material acetone charge, into the column bottoms and/or any other desired point to convert aldehydes to aldols. All the remaining components, including the acetone, are removed from the first rectification column as the bottom fraction and are fed to the second rectification column. Commercial (purified) acetone is recovered from the top of the second rectification column, while residual aldols, water, and other high-boiling impurities (cumene, alpha-methyl-styrene) are removed from the second column as the bottom fraction and are sent for subsequent processing or purification as desired. An alkaline reagent is also fed to the second rectification column. The alkaline reagent is fed to the second rectification column at a point above the feed from the first rectification in order to remove any residual aldehydes by condensation to aldols.

An alkaline reagent is supplied to both columns. It is desirable to add the alkaline reagent to the feed and/or to the bottom portion in the first column, and to a point above the feed supply tray in the second column. The alkaline reagent may be the same or different in the two columns.

Any organic or inorganic base, specifically a base that is water soluble, may be used as the alkaline reagent. Specific examples of alkaline reagents include, but are not limited to, carbonates and hydroxides of alkaline metals, such as sodium hydroxide and potassium hydroxide, sodium phenate, and amines and polyamines (such as ethylenediamine and tetraethylenepentamine), specifically sodium hydroxide. The alkaline reagent may be an aqueous solution, and in some embodiments, at least about a 20% aqueous solution. Other aqueous solutions may be used but the amounts of water may affect the amounts used and the efficiency of the columns.

Since acetone raw material generally contains an increased quantity of unsaturated impurities such as, for example, unsaturated carbonyl-containing compounds and the like, an oxidative reagent is used for the more effective removal of these impurities during the distillation process. The oxidative reagent is added to the first column, preferably to the lower portion of the first column.

Organic or inorganic oxidizers and, specifically, organic or inorganic peroxides, may be used as the oxidative reagent. Examples of oxidative reagents include, but are not limited to, hydrogen peroxide, methylhydroperoxide, and cumene hydroperoxide and any other inorganic oxidizers such as potassium permanganate, sodium peroxide and sodium percarbonate, specifically hydrogen peroxide, methylhydroperoxide, and cumene hydroperoxide, more specifically hydrogen peroxide. The oxidative reagent may be used in the form of an aqueous reagent at 0.1 to 30 wt %.

In chemical oxidation of this type, the low-boiling components and unsaturated carbonyl impurities are converted to their high-boiling derivatives (which are generally organic acids), which are soluble in water and resistant to thermal decomposition. These high-boiling derivatives are removed in the bottom fraction of the first column, which is then fed to the second column. The high-boiling derivatives are then removed from the second column as the bottom fraction and sent for further processing, separating or disposal. Since the impurities are converted to organic acids by addition of the oxidative reagent rather than aldols, there is no re-conversion to aldehydes.

Optimum removal of aldehydes and unsaturated impurities is best achieved when the selected ratio between the alkaline and oxidative reagents is used. They are most efficiently removed when the selected ratio of reagents is used; use of excess reagents may still remove the impurities, but this will result in an inefficient and/or less cost effective operation of the process.

The "KT-test" (permanganate test for time, an oxidation test using a solution of potassium permanganate) is widely used as an analytical test for determining the total quantity of aldehydes and other reducible impurities contained in commercial acetone. A large percentage of the acetone currently sold commercially on the market has a minimal KT-test value equal to about 2 hours. Using the method of the invention, it is possible to produce commercial (purified) acetone which has a KT-test time greater than 8 hours, specifically at least 8.5 hours.

Another quality indicator is the measured level of aldehyde, specifically acetaldehydes, in the commercial acetone, and a desirable level is less than 10 ppm, specifically less than 8.1. In some cases, there may be other important indicators of quality for commercial acetone, such as, for example, the water and diacetone alcohol content of the acetone.

Referring to the FIGURE, which is a process flow diagram of a two column rectification (or purification) process, the acetone raw material charge 2 is fed to the first rectification column 1, where the top fraction 4 or low-boiling acetone impurities, are isolated and removed from the first column. An alkaline reagent 3, such as sodium hydroxide, is also fed to the first column 1 to convert the residual aldehydes, α,β-unsaturated carbonyl-containing compounds and other remaining impurities to high-boiling components. An oxidative reagent 10 (that is effective for oxidizing aldehydes to organic acids), such as hydrogen peroxide, is also fed to the first column 1. After removal of the top fraction 4 (also referred to as a low molecular weight purge), the remaining column contents 5 are fed to the second rectification column 6. In the second column 6, the acetone is cleansed of any residual aldols, water and other high-boiling impurities and is removed in the form of a distillate 8. The alkaline reagent 7 is also fed to the second rectification column 6 above the charge tray to remove residual aldehydes and other impurities. It is desirable to maintain a specific weight ratio of alkaline reagent (such as sodium hydroxide) to oxidative reagent (such as hydrogen peroxide), such as 1:0.1 to 1:100, and from 1:0.5 to 1:10.

The method is illustrated by the following non-limiting examples.

EXAMPLES

The following test procedures were used to determine the KT-Test values and the amount of acetaldehyde in the acetone.

Permanganate Test Procedure (KT-Test) (Also Referred to as the "SABIC KT-Test")

A graduated glass cylinder (50 ml) was filled with a sample of commercial acetone to the 50 ml mark. A 2 ml sample of a 0.02 wt % aqueous solution of potassium permanganate was added to the acetone sample and the solutions mixed well. The cylinder containing the acetone/potassium mixture was placed in a water bath maintained at 25° C. The color of the acetone/potassium permanganate mixture was observed every 30 minutes for loss of the red-purple color. The KT-Test value was determined by the number of hours required for the acetone/permanganate solution to fade to the orange-pink color of a standard color solution (prepared by dissolving 0.280 grams of uranyl nitrate hexahydrate and 0.170 grams of cobaltous chloride hexahydrate in 50 ml of distilled water).

Acetaldehyde Test Procedure

A GC HP5890 gas chromatograph equipped with a dual FID detector and using a 1 m by 5 mm (outside diameter) glass column packed with Cromosorb 102 on 80/100 Supelcoport measured acetaldehyde content in commercial acetone samples. The gas chromatogram operating conditions included an oven temperature of 120° C., an injector temperature of 200° C., a detector temperature of 250° C. with an argon flow of 30 ml/min, a hydrogen flow of 30 ml/min and air flow of 300 ml/min. Total sample run time was 10 minutes. The acetaldehyde content in commercial acetone samples was determined from a calibration curve obtained by injecting 1.0 micro liter control samples of standard mixtures of acetaldehyde free acetone and freshly distilled acetaldehyde containing 5, 10, 20, 40, 70 and 100 ppm of acetaldehyde in acetaldehyde-free acetone.

Three examples and two comparative examples were run to illustrate the invention. The operating parameters and a summary of the results from the runs are shown in Tables 1 and 2 below.

Comparative Example 1

CEx.1

Crude acetone obtained from the process of producing phenol from cumene containing up to 65 wt % of acetone and a corresponding quantity of water, cumene and alpha-methyl styrene was fed to a two-column laboratory purification system (as detailed in the FIGURE) for isolation and purification of acetone. The acetone also contained traces (at the level of ppm) of such compounds as acetaldehyde, propionaldehyde, methanol, mesityl oxide and other unsaturated carbonyls, as well as diacetone alcohol and phenol.

The crude acetone (raw material) 2 at a temperature of 50° C. was fed to the first rectification column 1, which was filled with Levin packing and had an efficiency of 38 theoretical trays (TT). The acetone charge was fed at theoretical tray 19 (as counted starting from the bottom of the column). A 20% sodium hydroxide (NaOH) aqueous solution 3 was fed into the column charge in an amount of 0.50 wt % of the column charge. The column operated at atmospheric pressure. While a temperature of 55 to 56° C. was maintained at the top of the column, and a reflux ratio of 50, the top fraction 4 was taken off in an amount of 1.5 to 2.0 wt % of the charge. The top fraction 4 contained a large percentage of low-boiling impurities including acetaldehyde. The temperature of the column reboiler was 67 to 68° C. The bottoms 5 of the first column was fed to the second rectification column 6 for subsequent processing in an amount of 98 to 98.5 wt % of the charge. The bottoms fraction contained acetone, cumene, alpha-methylstyrene, water and other impurities, including the products of aldol condensation.

The second rectification column 6 was also filled with Levin packing having an efficiency of 51.8 TT. The column operated at atmospheric pressure. The bottoms 5 were fed at theoretical tray 8 (counting from the bottom of the column). Purified commercial grade acetone was collected from the top of the column in the form of a vapor and was completely condensed, and the liquid portion was taken in batches as the end product 8, while the reflux was returned to the top of the column 6. The temperature at the top of the second column was kept at about 56° C. The two-phase bottoms product 9 from the second column 6 contained water, cumene and alpha-methylstyrene, traces of carbonyls, products of aldol condensation, phenol, phenolate and NaOH residues. The bottoms product 9 was collected from the column and was sent for further processing as desired.

Sodium hydroxide (NaOH) (20 wt % aqueous solution) 7 is also fed to the second column at theoretical tray 18 (counting from the bottom) in an amount of 0.05 wt % of the first column charge 2. The reflux number of the second column was kept at an average of about 2.0. The temperature in the second column was maintained about 101.9° C.

Comparative Example 2

CEx.2

Crude acetone raw material obtained from the cumene process was again purified. In Comparative Example 2, the NaOH (20 wt % aqueous solution) charge 7 was supplied to the second rectification column 6 at theoretical tray 18 in an amount of 0.10 wt % of the first column charge 2. The reflux number of the second column was kept at an average of about 2.0, and the temperature of the second column was kept at an average of about 101.5° C. All other conditions were the same as in Comparative Example 1.

Example 1

Ex.1

Crude acetone raw material from the cumene process was again purified. In Example 1, the NaOH (20 wt % aqueous solution) charge 3 was fed to the first column 1 in an amount of 0.10 wt % of the charge in the first column. In addition, a 5 wt % aqueous solution of hydrogen peroxide 10 was fed to the column in an amount of 0.15 wt % of the charge 2 to the column 1. NaOH (20 wt % aqueous solution) 7 was supplied at theoretical tray 18 of the second column 6 in an amount of 0.05 wt % of the charge 2. The reflux number of the second column was kept at an average of about 2.0. All other conditions were the same as in Comparative Example 1.

Example 2

Ex.2

Acetone raw material from the cumene process was again purified. In Example 2, the NaOH (20 wt % aqueous solution) charge 3 was fed to the first column 1 in an amount of 0.10 wt % of the charge in the first column. In addition, a 5 wt % aqueous solution of hydrogen peroxide 10 was fed to the column in an amount of 0.22 wt % of the charge 2 to the column 1. NaOH (20 wt % aqueous solution) 7 was supplied at theoretical tray 18 of the second column 6 in an amount of 0.05 wt % of the charge 2. The reflux number of the second column was kept at an average of about 2.0. All other conditions were the same as in Comparative Example 1.

Example 3

Ex.3

Acetone raw material from the cumene process was again purified. In Example 3, the NaOH (20 wt % aqueous solution) charge 3 was fed to the first column 1 in an amount of 0.15 wt % of the charge in the first column. In addition, a 5 wt % aqueous solution of hydrogen peroxide 10 was fed to the column in an amount of 0.20 wt % of the charge 2 to the column 1. NaOH (20 wt % aqueous solution) 7 was supplied at theoretical tray 18 of the second column 6 in an amount of 0.07 wt % of the charge 2. The reflux number of the second column was kept at an average of about 2.0. All other conditions were the same as in Comparative Example 1.

TABLE 2

Basic characteristics of purified (commercial) acetone

| Example | First column Top fraction $CH_3CHO$, ppm | Second column Purified acetone | | |
|---|---|---|---|---|
| | | $CH_3CHO$, ppm | SABIC KT-Test, (Hrs) | Water, wt %, (average value) |
| CEx. 1 | 868 | 8.1 | 8.5 | 0.07 |
| CEx. 2 | 756 | 9.5 | 8.0 | 0.05 |
| Ex. 1 | 3933 | 5.3 | 9.0 | 0.06 |
| Ex. 2 | 3224 | 4.5 | 10.5 | 0.05 |
| Ex. 3 | 2872 | 4.9 | 9.5 | 0.07 |

As shown by the Examples, the combination of an alkaline reagent and an oxidative reagent produces acetone at a higher purity level as shown by the KT-Test values and the amounts of residual acetaldehyde in the purified acetone than when only an alkaline reagent is used.

This method is a simple, economical method for producing high-quality (purified) commercial acetone that does not depend on the quality of the crude acetone raw material while also using the existing equipment. This will enable use of the method in chemical and other spheres of industry where removing impurities from the acetone is needed.

The singular forms "a," "an," and "the" include plural referents unless the context clearly dictates otherwise. Unless defined otherwise, technical and scientific terms used herein have the same meaning as is commonly understood by one of skill in the art to which this invention belongs. The modifier "about" used in connection with a quantity is inclusive of the stated value and has the meaning dictated by the context (e.g., includes the degree of error associated with measurement of the particular quantity). The terms "front", "back", "bottom", and/or "top" are used herein, unless otherwise noted, merely for convenience of description, and are not limited to any one

TABLE 1

Basic technological (operating) parameters

| | First column charge | | | | | Second column charge 20% solution of NaOH solution | | | |
|---|---|---|---|---|---|---|---|---|---|
| | 20% aqueous solution of NaOH | | 5% aqueous solution of $H_2O_2$ | | Top fraction | | Wt % of charge | | |
| Example | Wt % of charge | Point of feed | Wt % of charge | Point of feed | Reflux number | Wt % of charge | in first column | Point of feed | Reflux number | Column temperature, ° C. |
| CEx. 1 | 0.50 | Into Charge 2 | — | — | 50 | 2.0 | 0.05 | TT 18 | 2.0 | 101.9 |
| CEx. 2 | 0.50 | Into Charge 2 | — | — | 50 | 2.2 | 0.1 | TT 18 | 2.0 | 101.5 |
| Ex. 1 | 0.10 | Into Charge 2 | 0.15 | In column bottom 10 | 50 | 1.9 | 0.05 | TT 18 | 2.0 | 102.1 |
| Ex. 2 | 0.10 | Into Charge 2 | 0.22 | In column bottom 10 | 50 | 1.8 | 0.05 | TT 18 | 2.0 | 102.5 |
| Ex. 3 | 0.15 | Into Charge 2 | 0.20 | In column bottom 10 | 50 | 2.0 | 0.07 | TT 18 | 2.0 | 102.5 | position or spatial orientation. The endpoints of all ranges directed to the same component or property are inclusive and independently combinable (e.g., ranges of "less than or equal to about 25 wt %, or, more specifically, about 5 wt % to about 20 wt %," is inclusive of the endpoints and all intermediate values of the ranges of "about 5 wt % to about 25 wt %," etc.). The suffix "(s)" as used herein is intended to include both the singular and the plural of the term that it modifies, thereby including at least one of that term (e.g., the colorant(s) includes at least one colorants).

"Optional" or "optionally" means that the subsequently described event or circumstance can or cannot occur, and that the description includes instances where the event occurs and instances where it does not. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for purifying a crude acetone raw material containing low molecular weight impurities, using two columns in sequence consisting essentially of:
   (a) feeding the crude acetone raw material into a first rectification column;
   (b) adding an alkaline reagent and an oxidative agent into the first rectification_column to form high molecular weight impurities;
   (c) distilling a top fraction from the first rectification column whereby the top fraction is removed from the column to form a bottom fraction comprising an acetone mixture comprising high molecular weight impurities;
   (d) feeding the bottom fraction comprising the acetone mixture obtained in step c) to a second rectification column at a charge point on the column;
   (e) adding an alkaline reagent to the second column above the charge point of the bottom fraction fed in step d); and
   (f) separating a purified acetone from the high molecular weight impurities and distilling the purified acetone as a top fraction whereby the top fraction is removed from the second column,
   wherein the second rectification column is operated at atmospheric pressure, and wherein the purified acetone has an acetaldehyde level of less than 10 ppm as measured by gas chromatography from a calibration curve obtained using acetaldehyde/acetone standards and a permanganate test time of greater than 8.5 hours, as measured by the permanganate test method.

2. A method for purifying a crude acetone raw material containing low molecular weight impurities, using two columns in sequence consisting essentially of:
   (a) feeding the crude acetone raw material into a first rectification column;
   (b) adding an aqueous sodium hydroxide solution and an aqueous hydrogen peroxide solution into the first rectification column to form high molecular weight impurities;
   (c) distilling a top fraction from the first rectification column whereby the top fraction is removed from the column to form a bottom fraction comprising an acetone mixture comprising high molecular weight impurities;
   (d) feeding the bottom fraction comprising the acetone mixture obtained in step c) to a second rectification column at a charge point on the column;
   (e) adding an aqueous sodium hydroxide solution to the second column above the charge point of the bottom fraction fed in step d); and
   (f) separating a purified acetone from the high molecular weight impurities and distilling the purified acetone as a top fraction whereby the top fraction is removed from the second column,
   wherein the second rectification column is operated at atmospheric pressure, and wherein the purified acetone has an acetaldehyde level of less than 10 ppm as measured by gas chromatography from a calibration curve obtained using acetaldehyde/acetone standards and a permanganate test time of greater than 8.5 hours, as measured by the permanganate test method.

3. A method for purifying a crude acetone raw material containing low molecular weight impurities, using two columns in sequence consisting essentially of:
   (a) feeding the crude acetone raw material into a first rectification column;
   (b) adding an aqueous sodium hydroxide solution and an aqueous hydrogen peroxide solution into the first rectification column to form high molecular weight impurities;
   (c) distilling a top fraction from the first rectification column whereby the top fraction is removed from the column to form a bottom fraction comprising an acetone mixture comprising high molecular weight impurities;
   (d) feeding the bottom fraction comprising the acetone mixture obtained in step c) to a second rectification column at a charge point on the column;
   (e) adding an aqueous sodium hydroxide solution to the second column above the charge point of the bottom fraction fed in step d); and
   (f) separating a purified acetone from the high molecular weight impurities and distilling the purified acetone as a top fraction whereby the top fraction is removed from the second column,
   wherein the second rectification column is operated at atmospheric pressure, wherein the weight ratios of the sodium hydroxide solution to the hydrogen peroxide solution are between 1:0.5 to 1:10, and wherein the weight ratios of the sodium hydroxide solution in the first rectification column to the sodium hydroxide solution in the second rectification column are between 1:0.1 to 1:5, and wherein the purified acetone has an acetaldehyde level of less than 10 ppm as measured by gas chromatography from a calibration curve obtained using acetaldehyde/acetone standards and a permanganate test time of greater than 8.5 hours, as measured by the permanganate test method.

* * * * *